(12) United States Patent
Sugihara et al.

(10) Patent No.: US 6,288,527 B1
(45) Date of Patent: *Sep. 11, 2001

(54) TWO-DIMENSIONAL SENSOR USING LAPS FOR MEASURING CELL ACTIVITY

(75) Inventors: Hirokazu Sugihara, Katano; Makoto Taketani, Kyoto; Akihito Kamei, Nara; Hiroshi Iwasaki, Hirakata, all of (JP)

(73) Assignee: Matsushita Electric Industrial Co., Ltd., Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/661,314

(22) Filed: Jun. 13, 1996

(30) Foreign Application Priority Data

Jun. 20, 1995 (JP) .................................... 7-153343

(51) Int. Cl.[7] .................................................. G01N 27/00
(52) U.S. Cl. .................... 324/71.1; 324/444; 324/692; 324/72; 435/173.1; 436/63; 436/149; 436/806
(58) Field of Search .................... 324/44, 450, 452, 324/457, 458, 501, 752, 692, 71.1, 71.5, 72; 435/29, 173.1, 173.4; 436/63, 149, 806; 128/639, 734, 741; 204/402, 406

(56) References Cited

U.S. PATENT DOCUMENTS

| 3,448,377 | * | 6/1969 | Seiwatz et al. ........................ 324/501 |
| 4,704,576 | * | 11/1987 | Tributsch et al. ..................... 324/501 |
| 4,758,786 |   | 7/1988 | Hafeman ........................... 324/158 D |
| 4,855,243 | * | 8/1989 | Simic-Glavaski ....................... 436/63 |
| 4,963,815 |   | 10/1990 | Hafeman .............................. 324/715 |
| 5,496,697 | * | 3/1996 | Parce et al. ............................ 435/29 |
| 5,567,302 | * | 10/1996 | Song et al. ......................... 205/777.5 |
| 5,970,163 | * | 10/1999 | Iwasaki et al. ...................... 382/128 |
| 6,053,035 | * | 4/2000 | Nomura et al. ......................... 73/86 |

FOREIGN PATENT DOCUMENTS

| A-0 300 651 | 1/1989 | (EP) . |
| A-0 367 432 | 5/1990 | (EP) . |
| 06078889A | 3/1994 | (JP) . |
| 06296595A | 10/1994 | (JP) . |

OTHER PUBLICATIONS

Nakao et al., "Scanning–laser–beam semiconductor ph–imaging sensor", *Sensor And Actuators B*, No. 2/3, Jun. 1994, Lausanne, Ch, pp 119–123.

Baxter et al., "Microfabrication in silicon microphysiometry", *Clinical Chemistry*, vol. 40, No. 9, Sep. 1994, Washington, D.C., pp. 1800–1804.

* cited by examiner

*Primary Examiner*—Glenn W. Brown
(74) *Attorney, Agent, or Firm*—Morrison & Foerster, LLP

(57) ABSTRACT

A two-dimensional sensor is described including a substrate having a Si layer, a $SiO_2$ layer and a $Si_3N_4$ layer. On the surface of the Si back side, a thin film is formed by vapor deposition for making an effect electrode. On the surface of the $Si_3N_4$ front side, a fence is attached for containing a sample cell, culture medium and a reference electrode. This sensor is placed in an incubator and a bias voltage is applied between the effect and reference electrodes. When a high frequency modulated laser beam irradiates a spot on the back side of the sensor substrate, a signal of AC photocurrent is obtained from the effect electrode. This signal corresponds to a potential alteration due to the cell activity substantially at the spot. The signal is processed in a computer. Therefore, the beam spot size and location, corresponding to the size and the location of the measurement electrode, can be adjusted easily by focusing or moving the laser beam.

18 Claims, 6 Drawing Sheets

TWO-DIMENSIONAL SENSOR USING LAPS FOR MEASURING CELL ACTIVITY

FIELD OF THE INVENTION

The present invention relates to a two-dimensional sensor and a measurement system using the sensor for measuring cell activities.

BACKGROUND OF THE INVENTION

Medical research of nerve cells and research for the possibility of using nerve cells as electric devices are being made widely. When nerve cells become active, an action potential is generated. Ion density inside and outside of a nerve cell varies at first due to the alteration of the ion transparency, then the potential of the cell membrane alters. Therefore, it is useful to measure a two-dimensional distribution of the potential of the cell membrane for observing a sample cell or tissue. Measuring two-dimensional distribution of the potential provides a method for determining an active part and a level of the activity.

The inventors have developed an integrated combination electrode as the two-dimensional sensor that can be used for measuring cell membrane potentials of plural spots simultaneously without insertion of glass electrodes or other stimulating electrodes into the cell (Japanese Tokukaihei 6-78889, 6-296595). This integrated combination electrode includes many micro electrodes arranged in matrix and their lead pattern formed on a glass plate using conductive substances, on which a sample cell or tissue can be cultivated. This integrated combination electrode enables measuring potential alterations of plural spots in smaller pitch than glass electrodes or other conventional means. Furthermore, this integrated combination electrode enables long term observation of the sample cell or the tissue that are cultivated on the integrated combination electrode.

However, this integrated combination electrode is not suitable for an extensive use since it has a fixed size and a fixed pitch of measuring electrodes. In other words, it is difficult to use one integrated combination electrode for measuring different samples. In fact, different integrated combination electrodes were made by adjusting the size and pitch of electrodes to different samples.

SUMMARY OF THE INVENTION

A two-dimensional sensor and a measurement system using the sensor are described that are suitable for an extensive use of measuring cell activities of different samples, by improving the above integrated combination electrode and making the size and the pitch of the electrodes changeable.

The two-dimensional sensor according to the present invention has a substrate consisting of three layers made of Si, $SiO_2$ and $Si_3N_4$, a thin film formed by vapor deposition on the surface of the Si layer on the back side of the sensor substrate, for making an effect electrode, and a fence attached on the $Si_3N_4$ layer on a front side of the sensor substrate for containing a sample cell, culture medium and a reference electrode. When a light beam irradiates a spot on the back side of the sensor substrate, a signal is obtained corresponding to a potential alteration at the spot due to an activity of the cell placed in the fence on the sensor.

The two-dimensional sensor for measuring a cell activity according to this invention is based on a LAPS (Light-Addressable Potentiometric Sensor explained in U.S. Pat. Nos. 4,758,786 or 4,963,815) developed by Molecular Device CO., Ltd. in USA. As shown in FIG. 5, the LAPS comprises a semiconductor silicon substrate 101, oxide layer 102 and nitride layer 103 on the substrate. The LAPS is well known as a pH sensor for measuring pH of an electrolyte 104, such as liquid contacted with the LAPS. The principal of measuring pH of an electrolyte using LAPS will be explained briefly with reference to FIG. 5.

A bias voltage is applied to an EIS structure consisting of an Electrolyte 104, an Insulator and a Semiconductor, by using a potentiostat 105. A light beam modulated with a certain frequency is irradiated at a back side of the EIS structure. Then AC photocurrent flows as shown in FIG. 6. The time-voltage curve in FIG. 6 shifts along the horizontal axis (i.e., bias voltage) according to the pH value of the electrolyte. Therefore, the pH can be measured by detecting the AC photocurrent I under the condition where the predetermined bias voltage is applied. The reason that the I-V curve is shifted according to the pH of the electrolyte is considered as followed.

When the voltage is applied to the EIS structure, an energy band bending occurs at the interface between the semiconductor and the insulator. This energy band bending depends on pH of the electrolyte contacting with the insulator. In the surface of the insulator layer, silanol group (Si—OH) and amino group (Si—$NH_2$) are formed, and their functional groups combine with protons (H+) selectively, thus an equilibrium between the number of protons in the electrolyte and the number of combined protons is maintained. Therefore, if the pH of the electrolyte changes, electric charge on the insulator varies; then the energy band bending alters. As a result, a width of depletion layer between the semiconductor and the insulator alters. This alteration of the width, i.e., capacitance of the depletion layer causes alteration of the AC photocurrent. The LAPS also uses a photoconductive character of the semiconductor such that the electric conductivity increases by light irradiation.

In the same way as the LAPS, the two-dimensional sensor of the present invention comprises a substrate consisting of three layers made of Si, $SiO_2$ and $Si_3N_4$ as well as a thin film of an effect electrode formed by vapor deposition on the Si layer. The sensor of the present invention further comprises a fence for containing a sample cell, culture medium and a reference electrode. Two-dimensional distribution of the potential alteration generated by the activity of the cell placed in the fence is measured directly. In other words, the sensor of the present invention provides a potential generated directly by the activity of the cell contacted with the insulator layer. This mechanism is different from the pH sensor in the prior art using LAPS which generates a potential on the surface of the insulator by combining protons with the silanol group (Si—OH) and amino group (Si—$NH_2$) formed on the surface of the insulator as explained before.

The sensor of the present invention alters the width of the depletion layer between the semiconductor and the insulator. Thus a capacitance of the depletion layer alters. Moreover, electric conductivity at the spot irradiated by the light beam increases. As a result, a signal corresponding substantially to the potential alteration at the spot is obtained from the effect electrode.

The system for measuring a cell activity according to this invention comprises the above two-dimensional sensor, a light beam source for irradiating a spot on the back side of the two-dimensional sensor with a light beam, a DC power source for applying a DC bias voltage between the effect electrode on the back side of the two-dimensional sensor and the reference electrode in the fence on the front side, and means for processing a signal obtained between the two electrodes. It is preferable to use a laser beam source as the light beam source. The laser beam can be easily focused in a small spot, and the location of the beam spot can be controlled precisely. It is also preferable for the system to include means for maintaining an environment for cultivating the sample cell in the fence on the sensor, so as to enable a long-term observation.

In a preferred embodiment, the e system further comprises means for driving the laser with high frequency so as to emit a modulated high frequency laser beam, and the signal processing means detects an amplitude alteration of the AC photocurrent flowing between the effect electrode and the reference electrode. As mentioned before, the alteration of the width (capacitance) of the depletion layer between the semiconductor and the insulator due to the potential alteration generated by the activity of the cell contacted with the insulator is thus detected as the amplitude alteration of the AC photocurrent.

It is also preferable that the system further comprises means for scanning the laser beam emitted from the laser beam source, at high speed in the predetermined area of the back side of the two-dimensional sensor. Thus cell activities in plural spots are measured substantially at the same time. Instead of scanning one laser beam, a laser array that comprises a plurality of laser elements arranged in matrix can be used. By driving the plurality of laser elements with a time-sharing method, faster scanning can be performed. Alternatively, the system may comprise an X-Y stage that controls the horizontal position of the two-dimensional sensor for changing the spot location on the sensor that is irradiated by the laser beam.

DETAILED DESCRIPTION OF THE PREFERRED EMBODIMENTS

Figure 1:
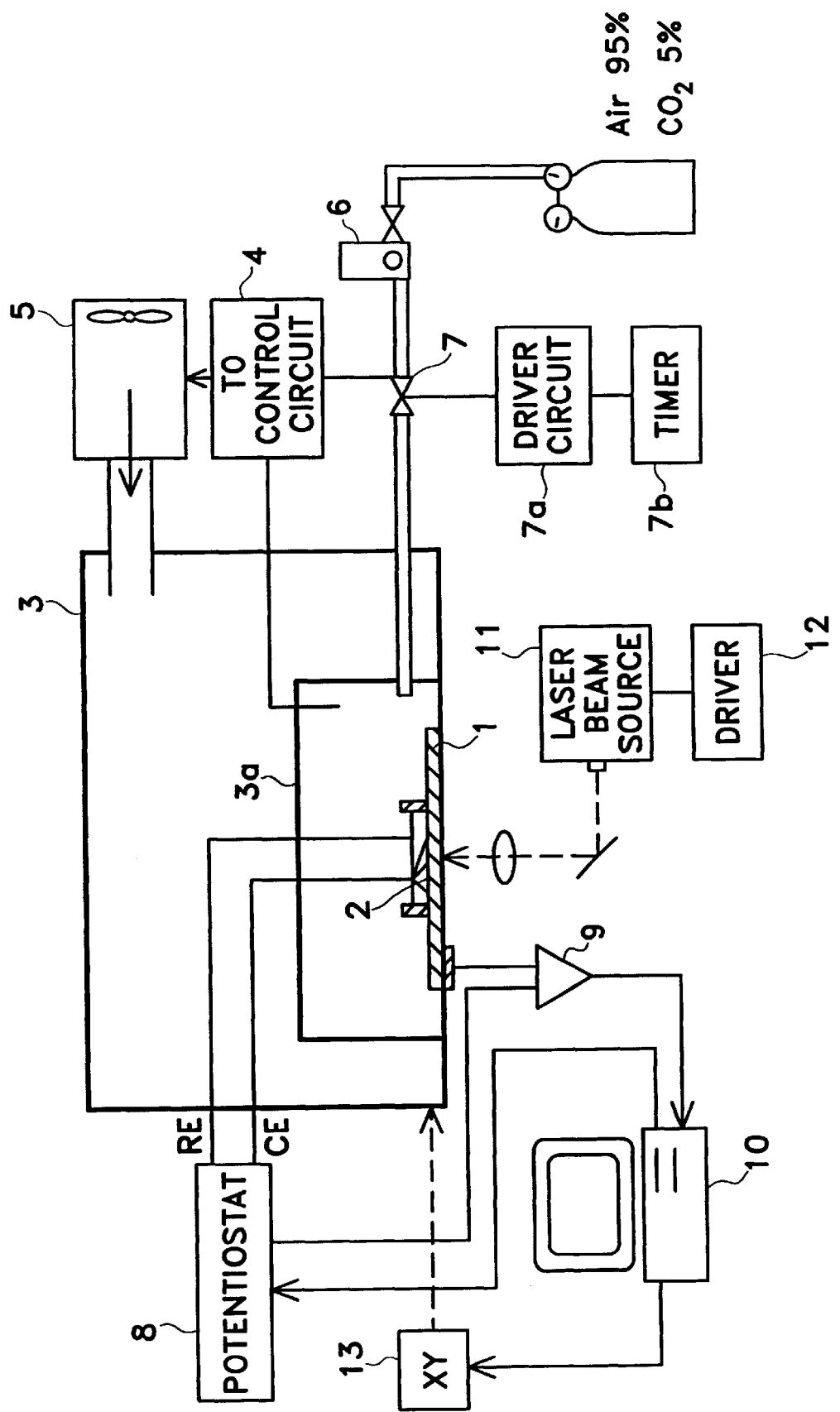
FIG. 1 is a block diagram of a cell activity measurement system using a two-dimensional sensor of the present invention.

FIG. 1 shows a preferred embodiment of the measurement system for measuring cell activities according to the present invention. The system has a two-dimensional sensor 1 for measuring cell activities, on which a sample cell 2 and its culture medium are placed. The two-dimensional sensor 1 including the sample 2 and the culture medium is set in an incubator 3.

Figure 2A:
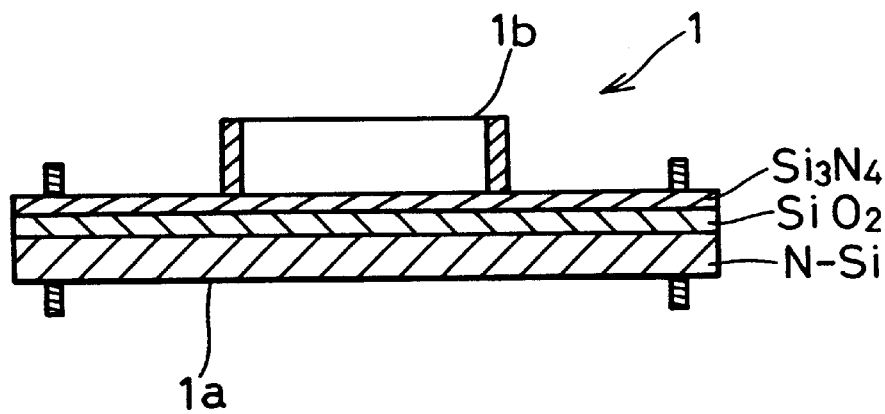
FIGS. 2A and 2B show a cross section and a plane view of the two-dimensional sensor used in the measurement system in FIG. 1.
Figure 2B:
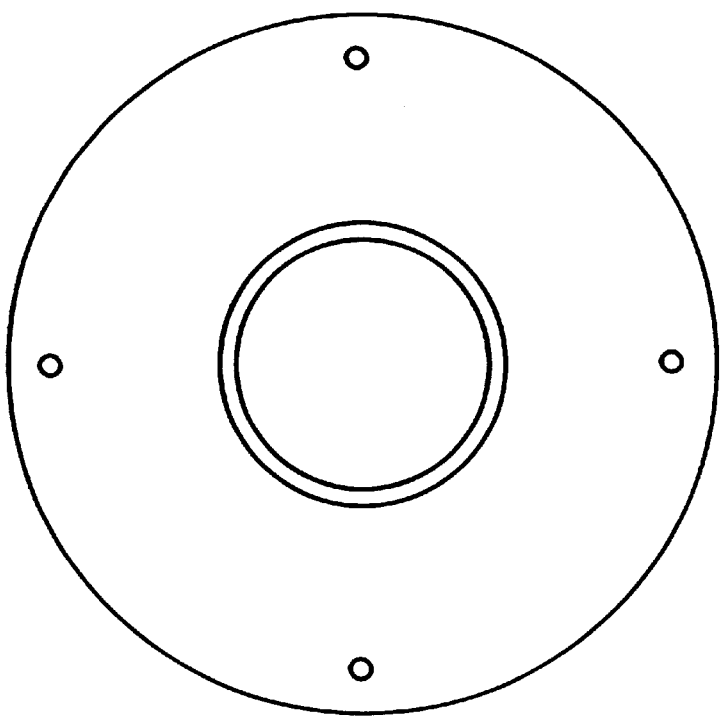

The two-dimensional sensor 1 comprise a three-layered substrate consisting of Si, $SiO_2$ and $Si_3N_4$, a gold-antimony thin film 1a as an effect electrode formed on the back side (Si side) of the substrate by vapor deposition, and a fence 1b formed on the front side ($Si_3N_4$ side) of the substrate for containing the sample cell, culture medium and a reference electrode, as illustrated in FIGS. 2A and 2B. FIG. 2A shows a cross section exaggerated in vertical direction. For example, total thickness of the sensor substrate is about 200 $\mu$m; the thickness of the $SiO_2$ layer is less than 50 nm; and the thickness of the $Si_3N_4$ layer is less than 100 nm. The Si substrate is N-channel type with resistance of 10 ohm·cm and thickness of 200 $\mu$m whose back side is also polished specularly. A gold-antimony thin film 1a formed on the back side by vapor deposition became an alloy at 500 degree Celsius to make an ohmic contact.

The silicon nitride layer ($Si_3N_4$) that is formed on the surface of the substrate is not toxic against a cell or other organic samples. Therefore it is suitable for cultivating a cell or other organic samples. The fence 1b attached to the surface of the $Si_3N_4$ layer for containing a cell or other samples has a cylindrical shape whose inner diameter is 26 mm and made of polycarbonate. Four bolts are attached to the two-dimensional sensor on four spots in its circular peripheral part for mounting on an aluminum frame.

In FIG. 1, the incubator part 3 has a double-wall structure for ensuring protection of the inside from infection by outside germs. A temperature control unit 4 controls a heater and a fan unit 5 according to an output of a temperature sensor, so as to maintain the sample room 3a of the incubator part 3 at a constant temperature of, e.g., 37±0.5° C. A mixed gas consisting of 95% air and 5% $CO_2$ is fed into the sample room. The conduit of the mixed gas has a flow meter 6 and an electromagnetic valve 7. The system has a drive circuit 7a for driving the valve 7 as well as a timer 7b that controls the drive circuit 7a. The incubator part 3, the temperature control unit 4, and other parts constitute the cultivating means.

The system includes a potentiostat 8 for applying a bias voltage between the reference electrode (RE) in the fence 1b of the sensor and the effect electrode on the backside of the sensor. The current signal between the above electrodes is led into an amplifier 9, which amplifies the signal and gives it to a computer 10 as the processing means. The computer includes a 16 bit A/D converter.

There is a correspond electrode (CE) within the fence of the sensor; the CE as well as the reference electrode (RE) is connected to the potentiostat 8. The CE is used for stimulating the sample by contacting the same in the fence of the sensor so as to measure an evoked potential generated by the sample. For this purpose, a pulse voltage is applied between the RE and the CE. This stimulating voltage (pulse voltage) is generated by the potentiostat 8 according to the instruction from the computer 10. The system can also measure a spontaneous discharge without applying any stimulations.

FIG. 1 further illustrates a laser beam source 11 and its driver 12 for emitting a laser beam to the backside of the two-dimensional sensor. The laser beam emitted from the laser beam source 11 is focused by an optical system including a mirror and a lens (an object lens of an inverted microscope was used). The beam may be focused into a spot having a diameter on the order of a micron. The laser source driver 12 includes a modulator that modulates the laser beam with a high frequency in the order of kilohertz.

The system further comprises means for changing a position of the laser-irradiated spot in the back side of the sensor; for example, an X-Y stage may be used that moves the two-dimensional sensor contained in incubator 3 in the horizontal direction. This X-Y stage can change the position of the irradiated spot by a step of 1 $\mu$m in the X-Y plane.

The position of the two-dimensional sensor 1 is changed while the position of the laser beam is fixed in the above embodiment. However, it is more preferable to scan the laser beam without moving the two-dimensional sensor 1. An X-Y galvano-mirror may be used in the optical system for scanning of the laser beam. An alternative method may use a laser array that consists of many laser elements arranged in a matrix. In this method, each laser element emits a laser beam perpendicularly to the backside of the sensor and the laser elements are driven with a time-sharing method.

Figure 3:
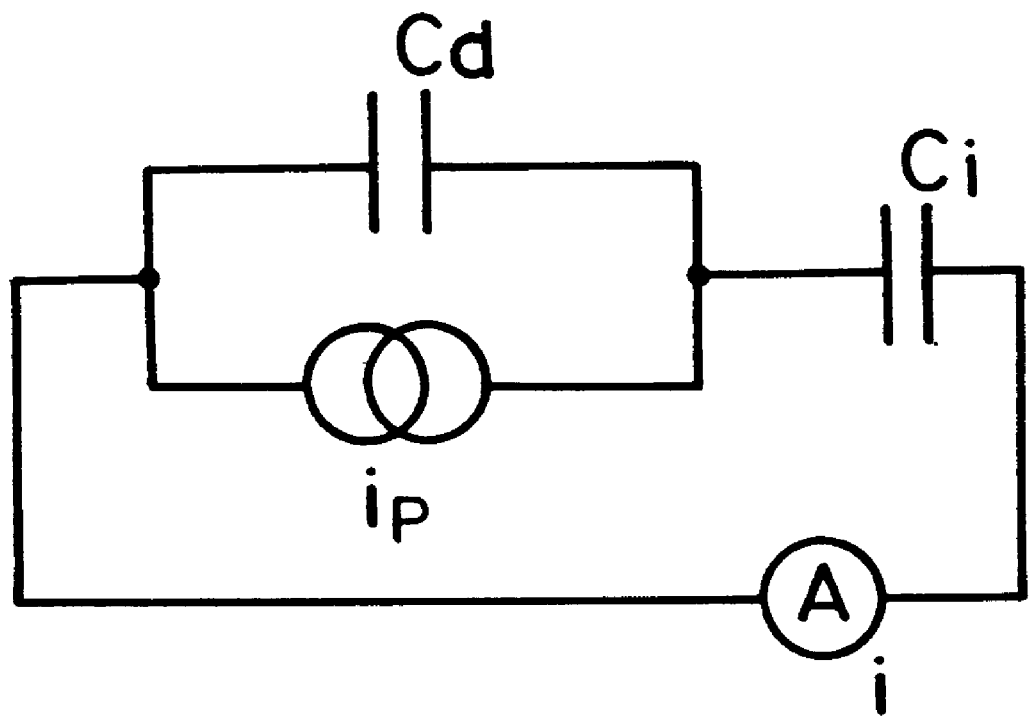
FIG. 3 illustrates an equivalent circuit of the circuit in which an AC photocurrent flows concerning the measurement system of FIG. 1.

As mentioned before, a laser-irradiated spot of the two-dimensional sensor 1 generates hole and electron pairs. Thus, a photocurrent is forced to flow by the bias voltage between the reference electrode and the effect electrode. A direct current does not flow since an insulator layer ($SiO_2$ and $Si_3N_4$) is formed on the surface of the two-dimensional sensor, while an alternate current flows as the laser beam is modulated with high frequency as mentioned before. When Ci is the capacitance of the insulator layer, Cd is the capacitance of the depletion layer between the semiconductor and the insulator, and iP is an AC photocurrent induced by the laser beam modulated with high frequency, then the AC photocurrent i is given by the following equation that is derived from the equivalent circuit (FIG. 3):

$$i = Ci \times iP/(Ci+Cd)$$

If a potential is generated on the surface of the insulator layer due to an activity of the cell contacted with the surface of the insulator layer, this potential makes an energy band bending at the interface of the semiconductor and the insulator. Consequently, some alteration occurs in the width of the depletion layer between the semiconductor and the insulator as well as the capacitance Cd of the depletion layer. Then the AC photocurrent i detected as mentioned with the above equation changes too. In the case that the N-type semiconductor is used for the sensor, the AC photocurrent decreases as the capacitance Cd increases if a positive potential has been generated on the surface of the insulator. On the other hand, if a negative potential has been generated, the AC photocurrent increases as the capacitance Cd decreases.

An experiment example will be explained as follows, where a nerve cell activity of a rat brain slice was monitored using the above measurement system. The brain of SD rat 2 days old were dissected; a part of a visual area of the brain was cut in a 0.5 mm thickness sample. This sample was cultured in the fence of the two-dimensional sensor. For enhancement of the adhesive property, the silicon nitride layer on the surface of the sensor was processed with polylysine and DF+f was used as the culture medium. 'DF' is a mixture of DMEM and F-12 Nutrient Mixture mixed by the ratio of 1:1; 'f' is a mixture of insulin 5 $\mu$g/ml, transferrin 100 $\mu$g/ml, progesterone 20 nM, hydrocortisone 20 nM, putresine 100 $\mu$M, selenium 20 nM, and fetal calf serum 5%.

Figure 4A:
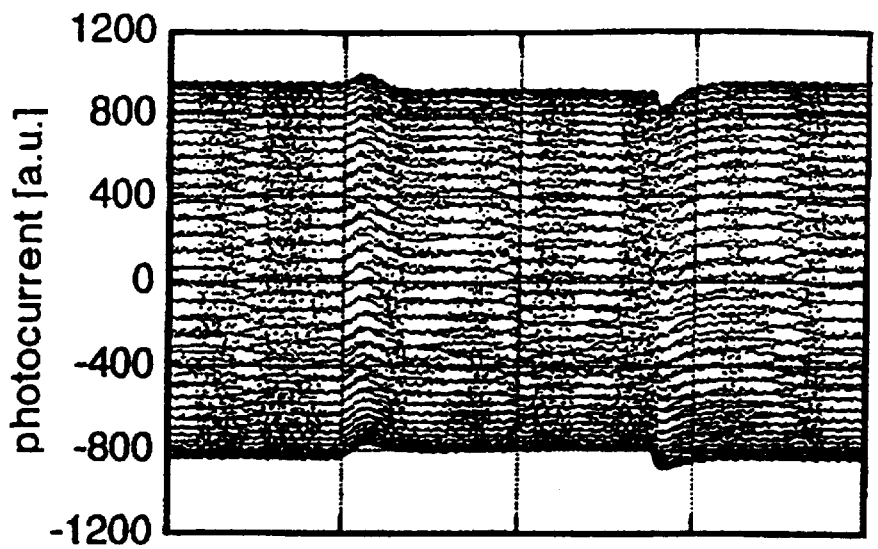
FIGS. 4A and 4B show a detected AC photocurrent and an alteration in the amplitude thereof as an example.
Figure 4B:
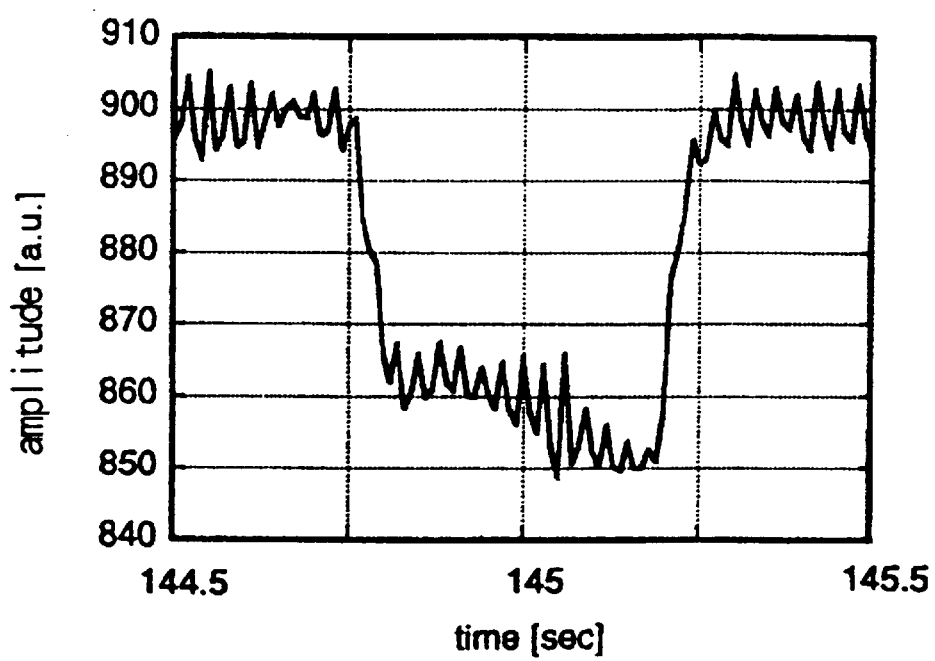
Figure 5:
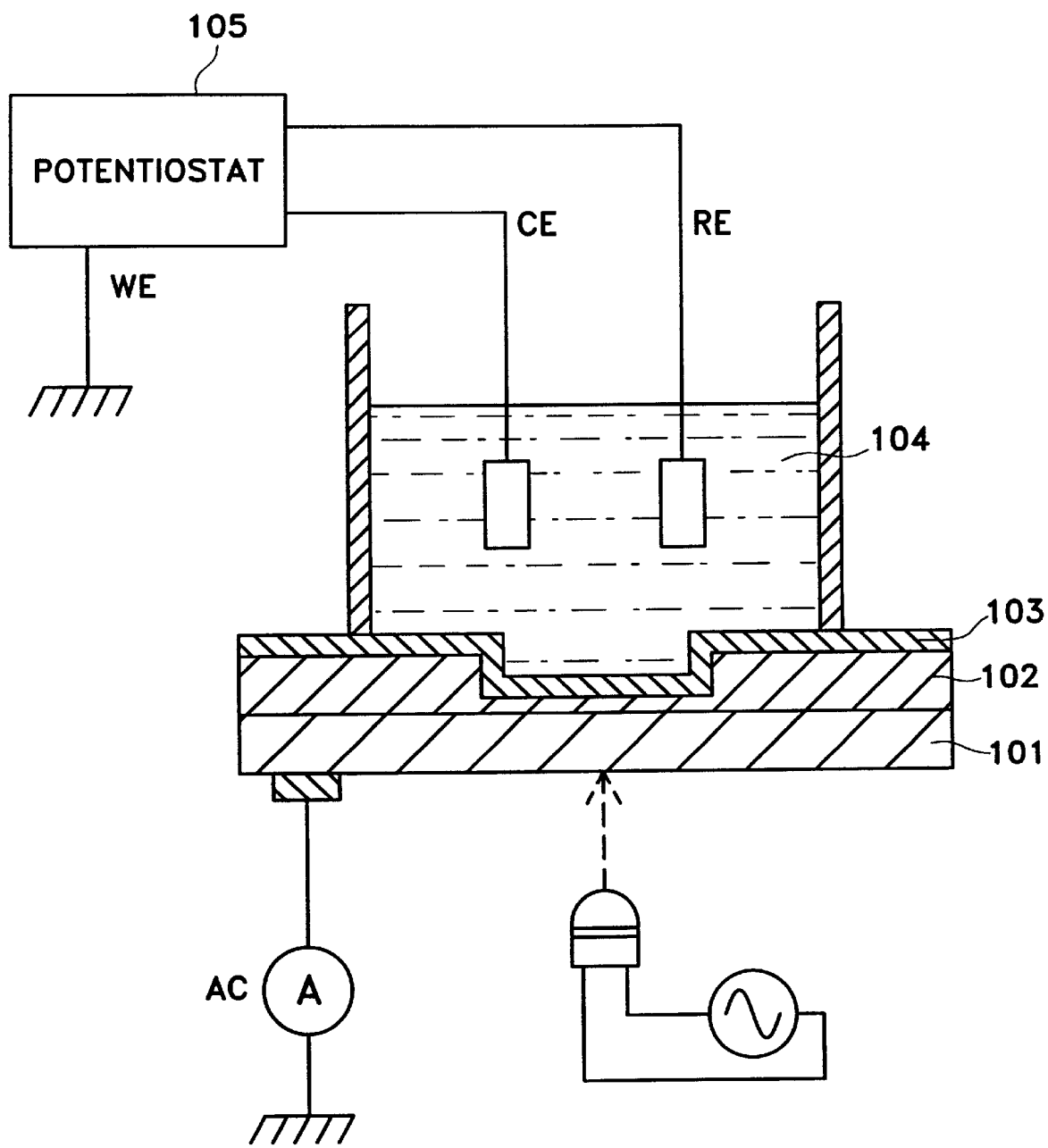
FIG. 5 illustrates a pH measurement system using LAPS in the prior art.
Figure 6:
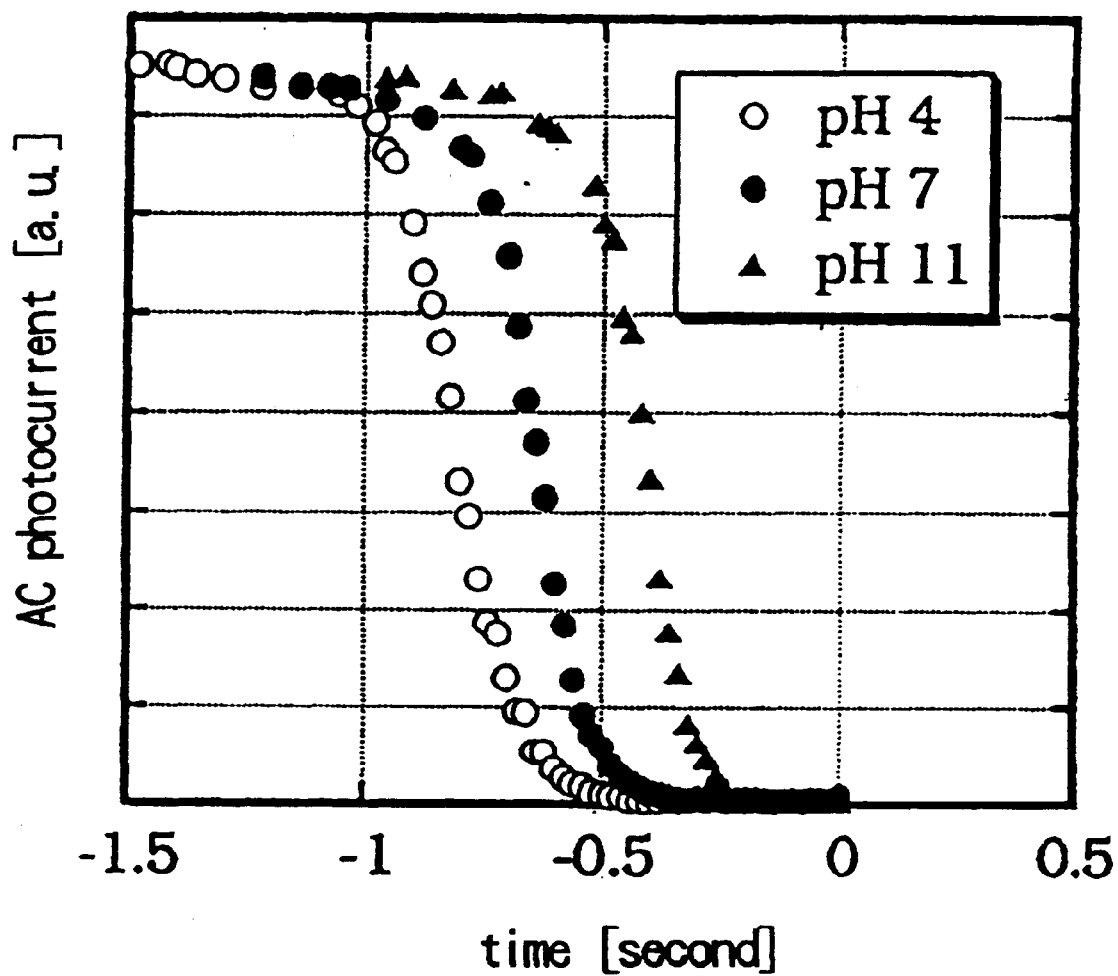
FIG. 6 is a graph showing a character of AC photocurrent versus bias voltage, obtained from the measurement circuit in FIG. 5, as well as a shift of this character.

The above sample generated a spontaneous discharge seven or ten days after starting of the cultivation. FIGS. 4A and 4B illustrate electric activities of the sample detected by the above measurement system. FIG. 4A shows an AC photocurrent digitized with 48 kHz; FIG. 4B shows an average valued wave form obtained by processing the current shown in FIG. 4A in every 10 ms. These figures teach that an amplitude of the AC photocurrent is decreased by 5% in the period between 144.8 and 145.2 second. Therefore, it can be supposed that a positive potential is generated on the surface of the insulator by the nerve cell activities. This decrease of the AC photocurrent amplitude was observed also in other parts of the sample that were considered to generate spontaneous discharges, when the location of the laser-irradiated spot is changed.

As explained above, the two-dimensional sensor of the present invention uses LAPS structure consisting of Si, $SiO_2$ and $Si_3N_4$ layers, on which a cell or tissue can be cultivated in the fence. By irradiating a spot on the back side of the sensor with a modulated laser beam, an electric potential alteration due to a cell activity in the spot is detected. Therefore, the beam spot size and location correspond to the size and the location of the measurement electrode respectively. Thus the size and the location of the measurement electrode can be changed easily by focusing or moving the laser beam relative to the sensor.

What is claimed is:

1. A measurement system for measuring electrical cell activity in a neural cell, the system comprising:
    a two-dimensional sensor, comprising:
        a sensor substrate having a thickness less than about 200 $\mu$m and comprising a Si layer being sufficiently thin that spontaneous electrical discharges from said neural cells are measurable, a $SiO_2$ layer, and a $Si_3N_4$ layer;
        an effect electrode comprising a thin film on a back side of the sensor substrate; and
        a fence disposed adjacent the $Si_3N_4$ layer on a front side of the sensor substrate for containing a sample cell, culture medium and a reference electrode;
    a high frequency modulated laser beam source for irradiating a spot on the back side of the sensor substrate with a laser beam;
    a DC power source for applying a DC bias voltage between the effect electrode on the back side of the sensor substrate and the reference electrode within the fence on the front side of the sensor substrate; and
    a processor for detecting variations in the amplitude of the AC photocurrent flowing between said effect and reference electrodes thereby measuring electrical cell activity;
    wherein an electrical signal is obtained from the effect electrode when said laser beam irradiates a spot on the back side of the sensor substrate, and wherein the electrical signal corresponds to a potential alteration substantially at the spot irradiated by said laser beam and to said electrical neural cell activity.

2. The measurement system according to claim 1, the system further comprising means for maintaining an environment for cultivating the cell in the fence on the sensor substrate.

3. The measurement system according to claim 1, the system further comprising means for driving the laser beam source with high frequency so that said high frequency modulated laser beam source emits a high frequency modulated laser beam.

4. The measurement system according to claim 1, the system further comprising means for scanning the laser beam emitted from the laser beam source in a predetermined area of the back side of the sensor substrate.

5. The measurement system according to claim 1, the system further comprising a laser array that includes a plurality of laser elements arranged in a matrix, each laser element emitting a laser beam perpendicularly to the back side of the sensor substrate.

6. The measurement system according to claim 1, the system further comprising an X-Y positioner coupled to said two-dimensional sensor for changing a location of the laser-irradiated spot on the sensor substrate.

7. The measurement system of claim 1 wherein said thin film is formed by vapor deposition.

8. A method for the measurement of active electrical activity in a tissue slice comprising the steps of:
   a.) providing a measurement system according to claim 1 for measuring electrical cell activity in a tissue slice,
   b.) placing a tissue slice upon said two-dimensional sensor,
   c.) irradiating a spot on the back side of the sensor substrate with said laser beam,
   d.) obtaining an electrical signal from the effect electrode corresponding to a potential alteration substantially at the spot irradiated by said laser beam and to said electrical tissue slice activity.

9. A measurement system for measuring electrical cell activity in a neural cell, the system comprising:
   a two-dimensional sensor, comprising:
      a sensor substrate having a thickness less than about 200 μm and comprising a Si layer being sufficiently thin that spontaneous electrical discharges from said neural cells are measurable, a $SiO_2$ layer and a $Si_3N_4$ layer;
      an effect electrode comprising a thin film on the Si layer on a back side of the sensor substrate; and
      a fence disposed adjacent the $Si_3N_4$ layer on a front side of the sensor substrate for containing a sample cell, culture medium and a reference electrode;
   a high frequency modulated laser array including a plurality of laser elements arranged in a matrix, each of said plurality of laser element adapted for emitting a laser beam perpendicular to the back side of the sensor substrate, for irradiating a single spot on the back side of the sensor substrate with said laser beam;
   a DC power source for applying a DC bias voltage between the effect electrode on the back side of the sensor substrate and the reference electrode within the fence on the front side of the sensor substrate; and
   a processor for processing an electrical signal obtained between the effect and reference electrodes;
   wherein said electrical signal is obtained from the effect electrode when said laser beam irradiates a spot on the back side of the sensor substrate and wherein the electrical signal corresponds to a potential alteration substantially at the irradiated spot and to said electrical neural cell activity in said neural sample.

10. The measurement system according to claim 9, the system further comprising means for maintaining an environment for cultivating the cell in the fence on the sensor substrate.

11. The measurement system according to claim 9, the system further comprising a high frequency modulator for modulating said laser array, wherein the processor detects an alteration in the amplitude of the AC photocurrent that flows between the effect and reference electrodes.

12. The measurement system according to claim 9, the system further comprising means for scanning the array emitted from the array source in a predetermined area of the back side of the sensor substrate.

13. The measurement system according to claim 9, the system further comprising an X-Y horizontal positioner coupled to said two-dimensional sensor for changing a location of said irradiated spot on the sensor substrate.

14. The measurement system of claim 9 wherein said thin film is formed by vapor deposition.

15. A method for the measurement of active electrical activity in a tissue slice comprising the steps of:
   a.) providing a measurement system according to claim 8 for measuring electrical cell activity in a tissue slice,
   b.) placing a tissue slice upon said two-dimensional sensor,
   c.) irradiating a spot on the back side of the sensor substrate with said laser beam,
   d.) obtaining an electrical signal from the effect electrode corresponding to a potential alteration substantially at the spot irradiated by said laser beam and to said electrical tissue slice activity.

16. A two-dimensional sensor for measuring electrical neural cell activity from a neural cell, comprising:
   a sensor substrate having a thickness less than about 200 μm and comprising a Si layer being sufficiently thin that spontaneous electrical discharges from said neural cells are measurable, a $SiO_2$ layer, and a $Si_3N_4$ layer;
   an effect electrode comprising a thin film on the Si layer on a back side of the sensor substrate; and
   a fence disposed adjacent the $Si_3N_4$ layer on a front side of the sensor substrate for containing a sample cell, culture medium, a reference electrode, and a correspond electrode;
   whereby a bias voltage is applied between the reference electrode and the effect electrode, and whereby a pulse voltage is applied between the reference and correspond electrode to stimulate the sample to generate an action potential, and wherein an electrical signal is obtained from the effect electrode when a laser beam irradiates a spot on the back side of the sensor substrate, and wherein the electrical signal corresponds to a potential alteration substantially at the spot irradiated by the laser beam and to said electrical neural cell activity.

17. The two-dimensional sensor of claim 16 wherein said thin film is formed by vapor deposition.

18. A method for the measurement of active electrical activity in a tissue slice comprising the steps of:
   a.) providing a two-dimensional sensor according to claim 13 for measuring electrical cell activity in a tissue slice,
   b.) placing a tissue slice upon said two-dimensional sensor,
   c.) irradiating a spot on the back side of the sensor substrate with said laser beam,
   d.) obtaining an electrical signal from the effect electrode corresponding to a potential alteration substantially at the spot irradiated by said laser beam and to said electrical tissue slice activity.

* * * * *